(12) United States Patent
Erbel

(10) Patent No.: US 7,400,700 B2
(45) Date of Patent: Jul. 15, 2008

(54) NON-DIAGNOSTIC STEREOSCOPIC X-RAY TRACKING OF MOVING OBJECTS IN THE CONTEXT OF RADIOTHERAPY AND RADIOSURGERY, WITH TIME-OFFSET IMAGE RECORDING

(75) Inventor: Stephan Erbel, Munich (DE)

(73) Assignee: BrainLAB AG, Feldkirchen (DE)

( * ) Notice: Subject to any disclaimer, the term of this patent is extended or adjusted under 35 U.S.C. 154(b) by 0 days.

(21) Appl. No.: 11/696,200

(22) Filed: Apr. 4, 2007

(65) Prior Publication Data
US 2007/0230655 A1    Oct. 4, 2007

Related U.S. Application Data

(60) Provisional application No. 60/745,032, filed on Apr. 18, 2006.

(30) Foreign Application Priority Data
Apr. 4, 2006   (EP)  ................................ 06007103

(51) Int. Cl.
*A61B 6/02* (2006.01)
(52) U.S. Cl. .......................... 378/41; 378/205
(58) Field of Classification Search .............. 378/41, 378/42, 205, 207
See application file for complete search history.

(56) References Cited

U.S. PATENT DOCUMENTS

| 5,207,223 | A | 5/1993 | Adler |
| 6,317,481 | B1 * | 11/2001 | Berestov ..................... 378/41 |
| 6,556,695 | B1 | 4/2003 | Packer et al. |
| 2002/0049375 | A1 | 4/2002 | Strommer et al. |
| 2002/0115923 | A1 | 8/2002 | Erbel |
| 2002/0122530 | A1 | 9/2002 | Erbel |
| 2003/0016781 | A1 * | 1/2003 | Huang ......................... 378/41 |
| 2003/0048868 | A1 | 3/2003 | Bailey et al. |
| 2004/0037390 | A1 | 2/2004 | Mihara et al. |

(Continued)

FOREIGN PATENT DOCUMENTS

DE    10 2004 030 836    1/2006

(Continued)

OTHER PUBLICATIONS

International Search Report for European Patent Application No. 06 00 7424 dated Sep. 13, 2006.

(Continued)

*Primary Examiner*—Hoon Song
(74) *Attorney, Agent, or Firm*—Renner, Otto, Boisselle & Sklar, LLP

(57) ABSTRACT

A non-diagnostic, stereoscopic x-ray tracking apparatus and method for tracking moving objects in the context of radiotherapy and radiosurgery includes using two x-ray tubes to alternately and repeatedly record x-ray images of an object along two different viewing lines through the target area of an irradiating apparatus. The viewing lines intersect at a known angle, wherein an extrapolated object trajectory is ascertained by determining surfaces and intersecting points. Further, a minimum transversal from the object trajectory onto a current viewing line is ascertained, wherein the three-dimensional position of the tracked object is approximated at the point at which the object trajectory meets the viewing line.

12 Claims, 3 Drawing Sheets

U.S. PATENT DOCUMENTS

2004/0042583 A1 3/2004 Wackerle et al.
2008/0037705 A1* 2/2008 Carrano et al. ................ 378/41

FOREIGN PATENT DOCUMENTS

EP 1 391 181 2/2004
EP 1 421 913 5/2004
EP 1 479 411 11/2004

OTHER PUBLICATIONS

International Search Report for European Patent Application No. 06 00 7103 dated Sep. 28, 2006.

* cited by examiner

NON-DIAGNOSTIC STEREOSCOPIC X-RAY TRACKING OF MOVING OBJECTS IN THE CONTEXT OF RADIOTHERAPY AND RADIOSURGERY, WITH TIME-OFFSET IMAGE RECORDING

RELATED APPLICATION DATA

This application claims priority of U.S. Provisional Application No. 60/745,032 filed on Apr. 18, 2006, which is incorporated herein by reference in its entirety.

FIELD OF THE INVENTION

The invention relates to the non-diagnostic, stereoscopic x-ray tracking of moving objects in the context of radiotherapy and radiosurgery. More specifically, the invention relates to x-ray tracking in which two x-ray tubes are used to repeatedly record x-ray images of an object along two different viewing lines through a target area of an irradiating apparatus, said viewing lines intersecting at a known angle.

BACKGROUND OF THE INVENTION

Real-time x-ray tracking of moving targets, for example implanted tracking markers, is known in principle in the context of radiotherapy and/or radiosurgery. Thus, for example, U.S. Pat. No. 5,207,223 describes a method and apparatus for selectively irradiating a target within a patient, wherein images of the target area and of a marker implanted in its vicinity are repeatedly taken using two x-ray image recording systems arranged at an angle to each other. The data obtained can be used to establish, in real time, where the marker and therefore the target area is actually situated at each point in time. This is particularly important for targets or target areas which move (for example movement of the target area with movement of the patient due to the patient's breathing). In this method, both x-ray image detecting units are actuated at the same time or substantially the same time. As a result, the two viewing lines for a moving object intersect in three-dimensional space at the same time and can be used to determine the detected position of the marker and/or target area for a particular point in time.

Given the high scanning rates used, which are necessary to precisely track the movement, such systems expose the patient to a relatively high radiation load when both x-ray systems are respectively activated at the same time.

SUMMARY OF THE INVENTION

A device and method in accordance with the invention can track a moving object within a patient, e.g., an object that changes its position with a patient's movement due to breathing. If, before therapy, imaging methods (e.g., CT, MR, etc.) are used to produce three-dimensional image recordings of the patient in the area around the target treatment region, wherein the object can also be seen or otherwise captured, the current location in three-dimensional space of these known patient structures can be determined using real-time tracking of the object and/or a marker or landmark. It is therefore possible to adapt irradiation to the movement of the object (movement of the patient, tracking the radiation device, and gating, where gating is the on/off switching of the x-ray beam at suitable points in time) and, thus, to avoid damaging healthy tissue and specifically irradiate diseased tissue.

For this purpose, a non-diagnostic, stereoscopic x-ray tracking method for tracking moving objects in the context of radiotherapy and radiosurgery is provided. In implementing the method, two x-ray devices (e.g., x-ray tubes) are used to repeatedly record x-ray images of an object along two different viewing lines through the target area of an irradiating apparatus, said viewing lines intersecting at a known angle, wherein:

a) the x-ray tubes are controlled such that one image is generated in each case, alternately using one of the two x-ray tubes; and with the assistance of a computer:

b) a surface is determined which is spanned by
   the viewing line from a first x-ray tube to the object in an image recorded at an earlier point in time and
   the viewing line from the first x-ray tube to the object in an image recorded at a later point in time;

c) an intersecting point is determined from
   a viewing line from the second x-ray tube to the object in an image recorded at a point in time between the earlier point in time and the later point in time, and
   the spanned surface;

d) another surface is determined, wherein the later point in time becomes a new earlier point in time, and wherein said other surface is spanned by
   the viewing line from the first x-ray tube to the object in an image recorded at the new earlier point in time and
   the viewing line from the first x-ray tube to the object in an image recorded at a new later point in time;

e) another intersecting point is determined from
   a viewing line from the second x-ray tube to the object in an image recorded at a point in time between the new earlier point in time and the new later point in time, and
   the other spanned surface;

f) a spatial straight connecting line R12, which connects the intersecting points, is calculated;

g) a minimum transversal between the connecting line R12 and the viewing line of the object at the new later point in time is calculated; and h) the three-dimensional position of the tracked object is approximated from the intersecting point of the minimum transversal and the viewing line at the new later point in time.

In simpler and more general terms, the method uses two x-ray tubes to alternately and repeatedly record x-ray images of an object along two different viewing lines, and an extrapolated object trajectory is ascertained by determining surfaces and intersecting points. The minimum traverse from the object trajectory onto a current viewing line is ascertained and the three-dimensional position of the tracked object is approximated at the point at which the object trajectory meets the viewing line.

This method enables the x-ray images to be detected at intervals in time and the position of the object to nonetheless be determined very precisely in real time with the aid of an approximation, even though the object will have moved during the time between the two x-ray recordings. Since the x-ray recordings are alternately produced using the two x-ray tubes of the system, only one tube is activated for each x-ray "shot" and the radiation load on the patient can be reduced by up to 50%, without reducing the temporal resolution of tracking, in particular along the main axis of movement of the object. In other words, a main portion of the x-ray recordings utilized for tracking is replaced with the suitable and intelligent use of image data and/or positional data that are available from the object and x-ray recordings (since the viewing lines are spatially known). Such intelligent data utilization, however, also incurs other advantages such as are discussed below.

The scatter radiation along one of the image recording axes of one of the x-ray systems does not impair the image production of the other x-ray system, since the two systems are not activated at the same time. This is in particular the case when the read-out times on the respective detectors are also time-offset. The maximum power consumption of the system as a whole is reduced, since it is no longer necessary to activate both x-ray tubes at the same time. Further, the overall power rating of the system is correspondingly reduced. Heating in the x-ray tubes, which represents a functional limitation for real-time tracking over longer periods of time, is reduced in relation to conventional systems as each tube is only actuated half as often. If necessary, the temporal resolution of the tracking system can be doubled, by actuating each tube/detector pair at its maximum possible frequency.

The dose reduction for the patient is highly important for radiotherapy and/or radiosurgery applications in which tracking has to be performed over long periods of time, since over the course of a complete treatment, the skin dose applied by the tracking x-ray irradiation may reach critical levels.

The time interval between generating an image using the first and second x-ray tube may be set such that one image is alternately generated using the first and second x-ray tube, at regular time intervals in each case. The tracked object can be a marking implant, in particular an implant that moves in correlation with the movement caused by breathing. It can, however, also be a body structure or body landmark that can be mapped using x-rays, in particular a structure or landmark that moves in correlation with the movement due to breathing. It is then possible to deduce from the movement of the implant and/or structure/landmark the movement of the surrounding body structures that are stored as a three-dimensional data set (CT, MR, etc.) in a navigation system connected to the system, such that the real-time location of the actual irradiation target can be known.

The object tracking is very precise if the minimum transversal (i.e., the shortest perpendicular from the straight connecting line onto the viewing line) is not too long. Preferably, the length of the minimum transversal is compared with a predetermined threshold value, wherein if the threshold value is exceeded, a state of imprecision is assumed. The method then can be adapted or modified, e.g., by increasing the scanning rate, which can be realized by reducing the time intervals between the images. It also is possible to output an error message that alerts the user to such a state of imprecision.

The invention also relates to a program which, when it is running on a computer or is loaded onto a computer, causes the computer to perform a method such as described here in various embodiments. The invention further relates to a computer program storage medium comprising such a program.

In accordance with another aspect of the invention, a stereoscopic x-ray tracking means for tracking moving objects in the context of radiotherapy and radiosurgery includes two x-ray tubes which repeatedly record x-ray images of an object along two different viewing lines through the target area of an irradiating apparatus, said viewing lines intersecting at a known angle. A control means alternately activates the x-ray tubes in order to generate one image in each case, respectively using one of the two x-ray tubes. Further, a computer-assisted image processing means implements the following:

a) a surface is determined which is spanned by
   the viewing line from a first x-ray tube to the object in an image recorded at an earlier point in time and
   the viewing line from the first x-ray tube to the object in an image recorded at a later point in time;
b) an intersecting point is determined from
   a viewing line from the second x-ray tube to the object in an image recorded at a point in time between the earlier point in time and the later point in time, and
   the spanned surface;
c) another surface is determined, wherein the later point in time becomes a new earlier point in time, and wherein said other surface is spanned by
   the viewing line from the first x-ray tube to the object in an image recorded at the new earlier point in time and
   the viewing line from the first x-ray tube to the object in an image recorded at a new later point in time;
d) another intersecting point is determined from
   a viewing line from the second x-ray tube to the object in an image recorded at a point in time between the new earlier point in time and the new later point in time, and
   the other spanned surface;
e) the spatial straight connecting line R12, which connects the intersecting points, is calculated;
f) the minimum transversal between the connecting line R12 and the viewing line of the object at the new later point in time is calculated; and
g) the three-dimensional position of the tracked object is approximated from the intersecting point of the minimum transversal and the viewing line at the new later point in time.

All the features described here, even if they are worded in terms of a method, can of course be implemented by corresponding devices and means.

Put slightly differently, the device and method also can be described as demonstrating a way of ascertaining three-dimensional coordinates of a moving object despite the deviations in the real-time projection lines. By calculating the surface determined by a projection line of the object in one image and by its direct predecessor, and by calculating the intersecting point between this surface and a viewing line and/or projection line of the same object, detected from the other viewing angle (e.g., by the other x-ray tube) at a point in time between the two aforesaid image detections, it is possible to determine a three-dimensional point. This reconstructed three-dimensional point is an approximation of the actual position of the object at said predetermined point in time. The precision of this reconstruction depends on the linearity of the 3D movement of the object. This reconstructed point, however, corresponds to a point in time in the past, and because of this difference in time, real-time tracking is thus still not possible. If, however, the reconstruction of a 3D point as described above is performed again in sequence, two 3D points are obtained, each on a projection line of an x-ray unit.

A line through these two reconstructed points would approximate the movement trajectory of the object through three-dimensional space. One problem here is that such a movement trajectory often does not allow the real-time location to be determined for the point with sufficient precision, in particular when movements are non-linear and/or change over time. FIG. 3 shows curves for an actual breathing signal (the curve of points) and for an extrapolated breathing signal (the curve of triangles). The external vertical abdominal movement in millimeters is plotted against the time axis, and it is clear from these two representations how imprecise an extrapolated breathing curve can be as compared to the actual movement of breathing.

Returning now to the movement trajectory of the object as approximated by two points, it is then clear that such an approximated trajectory alone cannot yet provide good results or a good approximation for real-time tracking.

Additional information can be provided from the applied steps, namely actual real-time information on the position of the object, since the object lies directly on the viewing line of the last x-ray projection used for spanning the surface, precisely at the point in time of the x-ray image thus produced. This information can be utilized to very precisely approximate the exact position of the object for the last point in time at which a projection viewing line is provided, and to this end, the shortest distance between the movement trajectory and the last viewing line is determined by a perpendicular line onto the viewing line. This perpendicular line is the so-called minimum transversal. Where the minimum transversal (i.e. the shortest (perpendicular) connection between the two straight lines mentioned which are skewed with respect to each other) meets the last projection viewing line, there is in turn a point and it is precisely this point which lies at a very good approximation of the actual real-time position of the object, i.e., at the time at which the last x-ray viewing line was produced in order to span the surface.

The precision of the method will vary somewhat depending on the linearity of the movement of the object. Specifically, for moving objects such as implanted radio-opaque markers, which are conventionally used for radiotherapy tracking, a main axis of movement can be determined which for implants in the lung, liver or kidneys is typically a movement along the longitudinal axis of the body. In these cases, it is specifically important to have a good spatial/temporal resolution for the object along this direction. The viewing lines of the two x-ray units (x-ray detectors) preferably intersect these main axes of movement at a large enough angle that the main movement component can be equally well detected in images from both x-ray source/detector pairs.

BRIEF DESCRIPTION OF THE DRAWINGS

The forgoing and other features of the invention are hereinafter discussed with reference to the drawing.

DETAILED DESCRIPTION

Figure 1:
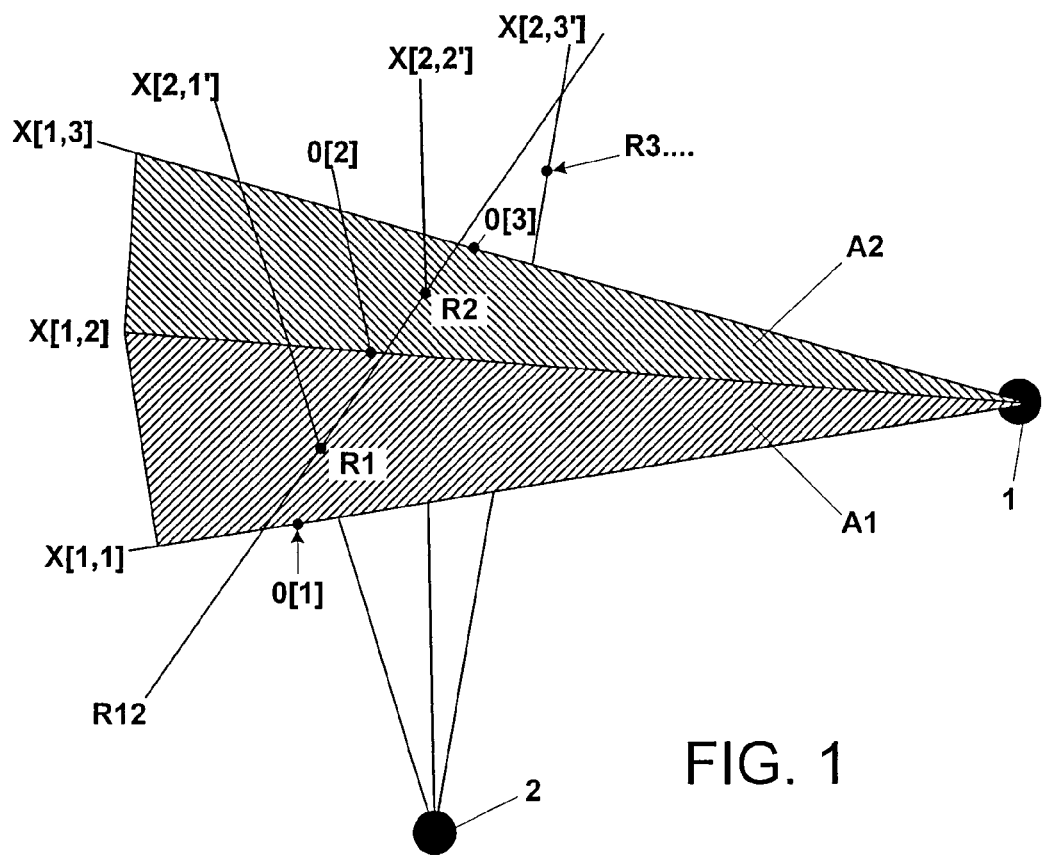
FIG. 1 is an exemplary schematic representation of the acquisition of the points and surfaces for x-ray tracking in accordance with the invention.

FIG. 1 shows two x-ray sources 1 and 2, and an object O that moves through a number of successive points in time, i.e., the object O[1] at Time 1, the object O[2] at Time 2 and the object O[3] at Time 3. The position of the object is tracked as follows:

At Time 1, a first x-ray image is produced using the x-ray source 1, and a viewing line X[1, 1] in this x-ray image passes through the object O[1]. The object then moves on and at Time 2 comes to the point at which it is shown by 0[2]. An x-ray image is in turn also produced at this point in time by the source 1, and the viewing line X[1, 2] is obtained.

Between Time 1 and Time 2 (in this example, after half the time has passed), i.e., at the intermediate point in time 1', an x-ray recording is produced using the x-ray source 2 and having the viewing line X[2, 1']. If the surface A1 between the viewing lines X[1, 1] and X[1, 2] is then calculated and/or spanned, it is also possible to calculate the point at which the object viewing line X[2, 1'] from the x-ray source 2 penetrates the surface A1 at the intermediate point in time 1', and the point R1 is obtained. This intersecting point R1 can be regarded as a first approximately reconstructed point on the trajectory of the object, but this information is only valid for a point in time in the past, since the object already has moved to point O[2].

However, the information on R1 can nonetheless be used if the present sequence is performed again, i.e., at Time 3, the viewing line X[1, 3] is in turn recorded using the x-ray tube 1, wherein the point O[3] lies on the viewing line X[1, 3] at Time 3. If an image is then recorded using the x-ray tube 2 and having the viewing line X[2, 2'] for the intermediate point in time 2', and the point R2 at which the viewing line X[2, 2'] penetrates the surface A2 (the surface between X[1, 2] and X[1, 3]) is in turn determined, then one already has two extrapolated points R1 and R2 and can thus determine an approximated movement trajectory for the object. This approximated movement trajectory is shown by R12 in FIG. 1 and is a straight line through R1 and R2. In order to further continue the approximate movement trajectory, these procedures can be repeated, and therefore the viewing line X[2, 3'] is also indicated, on which the point R3 would then lie. The procedure is continued in this sequence.

Since the linear approximation of the movement trajectory R12 can be relatively inadequate, as follows from the deviations in the actual and extrapolated breathing curve in FIG. 3 and as has already been described above, it would be possible to determine the real-time object point on the basis of the movement trajectory R12, but only imprecisely. The method, however, recognizes that information is already available in the demonstrated procedure that allows the precision to be improved, namely the information that the object O lies precisely on the viewing line X[1, 3] at Time 3. This information can then be intelligently evaluated; for the explanation, reference is made to FIG. 2.

Figure 2:
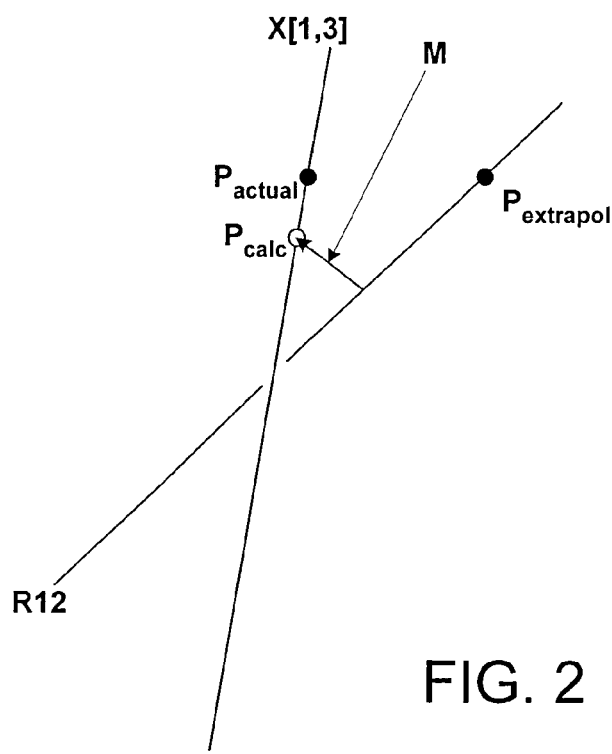
FIG. 2 is an exemplary schematic representation of the determination of the real-time location of the object with the aid of a minimum transversal in accordance with the invention
Figure 3:
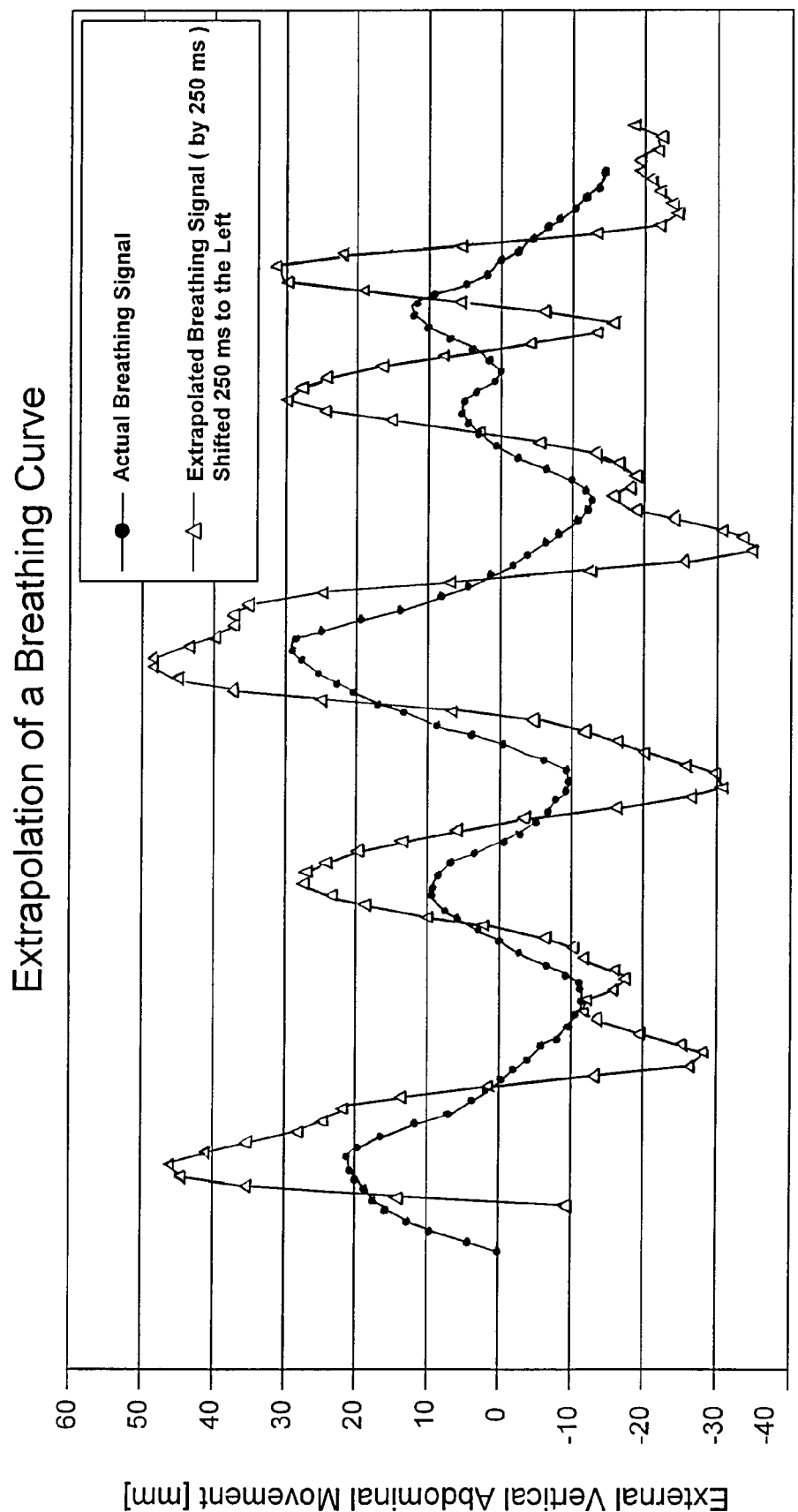
FIG. 3 is an exemplary graphic representation showing the deviation between an extrapolated and an actual breathing curve.

FIG. 2 shows the movement trajectory R12 again. The point $P_{extrapol}$, which would result if the position of the object at Time 3 were merely calculated as a continuation on this movement trajectory, is shown once on the movement trajectory R12, for comparison. The actual calculation, however, takes a different route, by processing the information that the actual object location $P_{actual}$ must lie on the viewing line X[1, 3]. Although it is not possible to use this one projection to exactly establish the location of the point $P_{actual}$ on the length of X[1, 3], the information on the position of this viewing line, however, can be evaluated by calculating a minimum transversal M between the two skewed straight lines R12 and X[1, 3]. The minimum transversal is the shortest spatial distance between the two straight lines and intersects the two straight lines perpendicularly. The point $P_{calc}$ results where the minimum transversal M intersects the viewing line X[1, 3], and this point $P_{calc}$ is a very good approximation of the actual position of the point $P_{actual}$ As a result, the point $P_{calc}$ is thus a very good approximation of the real-time position of the object O at Time 3.

The object tracking described herein is thus able to realize a very good approximation of the position and/or determination for an object, at a substantially reduced radiation load and with the other advantages mentioned above.

Figure 4:
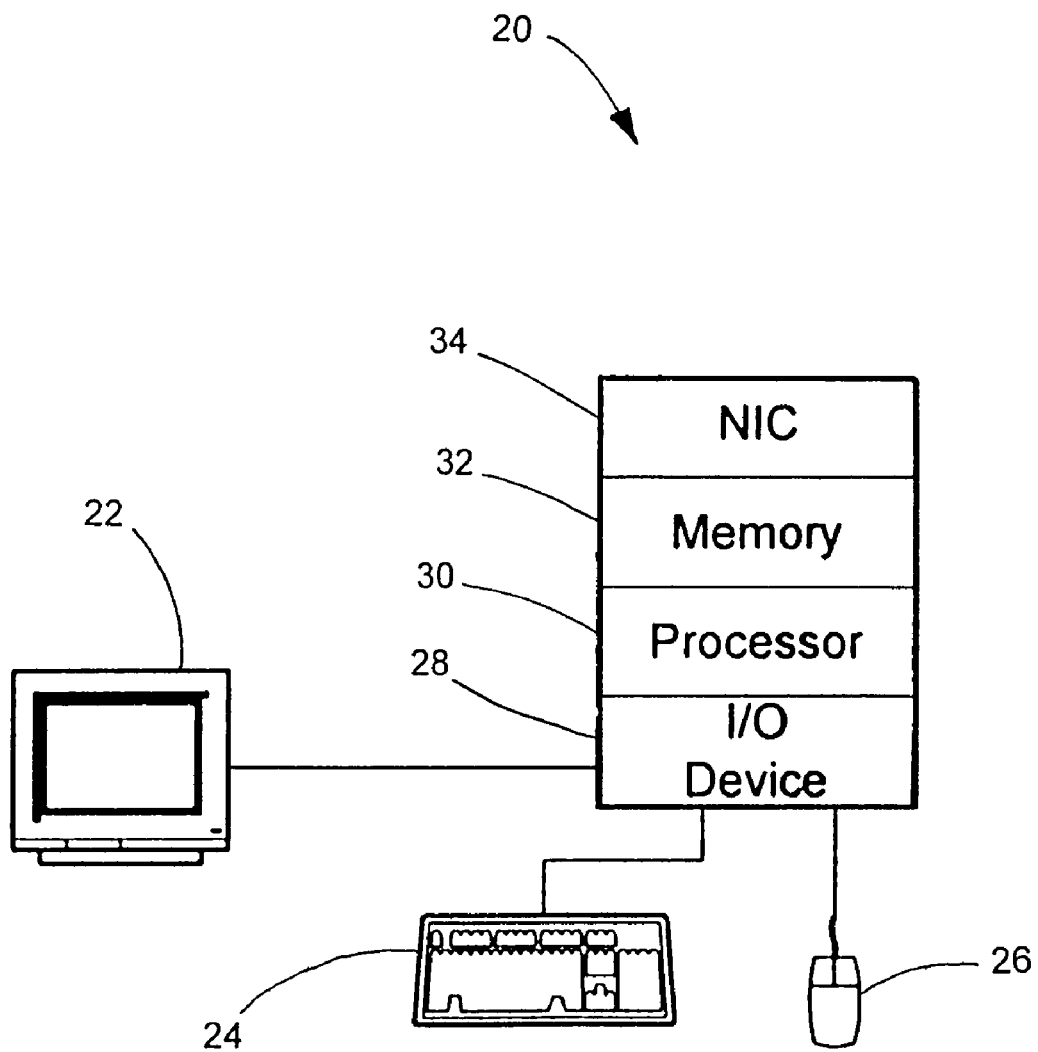
FIG. 4 is a block diagram of an exemplary computer system that can be used to carry out the method in accordance with invention.

FIG. 4 illustrates a computer system 20 that may be used to implement the method described herein. The computer system 20 may include a display 22 for viewing system information, and a keyboard 24 and pointing device 26 for data entry, screen navigation, etc. A computer mouse or other device that points to or otherwise identifies a location, action, etc., e.g., by a point and click method or some other method, are examples of a pointing device 26. Alternatively, a touch screen (not shown) may be used in place of the keyboard 24 and pointing device 26. The display 22, keyboard 24 and mouse 26 communicate with a processor via an input/output device 28, such as a video card and/or serial port (e.g., a USB port or the like).

A processor 30, such as an AMD Athlon 64® processor or an Intel Pentium IV® processor, combined with a memory 32 execute programs to perform various functions, such as data entry, numerical calculations, screen display, system setup, etc. The memory 32 may comprise several devices, including volatile and non-volatile memory components. Accordingly, the memory 32 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 30 and the memory 32 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 34 allows the computer system 20 to communicate with other devices.

A person having ordinary skill in the art of computer programming and applications of programming for computer systems would be able in view of the description provided herein to program a computer system 30 to operate and to carry out the functions described herein. Accordingly, details as to the specific programming code have been omitted for the sake of brevity. Also, while software in the memory 42 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A non-diagnostic, stereoscopic x-ray tracking method for tracking moving objects in the context of radiotherapy and radiosurgery, wherein first and second x-ray devices are used to repeatedly record x-ray images of an object along two different point of views through a target area of an irradiating apparatus, said two different point of views intersecting at a known angle, comprising:

controlling the first and second x-ray devices such that each x-ray device alternately obtains an image of the object as the object moves through the target area, and with the assistance of a computer determining a first surface that is spanned by a first viewing line from the first x-ray device to the object in an image recorded at an earlier point in time and a second viewing line from the first x-ray device to the object in an image recorded at a later point in time;

determining a first intersecting point from a third viewing line from the second x-ray device to the object in an image recorded at a point in time between the earlier point in time and the later point in time, and the first spanned surface;

determining a second surface, wherein the later point in time becomes a new earlier point in time, and wherein said second surface is spanned by the second viewing line from the first x-ray device to the object in an image recorded at the new earlier point in time and a fourth viewing line from the first x-ray device to the object in an image recorded at a new later point in time;

determining a second intersecting point from a fifth viewing line from the second x-ray device to the object in an image recorded at a point in time between the new earlier point in time and the new later point in time, and the second spanned surface;

calculating a spatial straight connecting line that connects the first and second intersecting points;

calculating a minimum transversal between the spatial straight connecting line and the fourth viewing line of the object at the new later point in time; and approximating a three-dimensional position of the tracked object from an intersecting point of the minimum transversal and the fourth line of site at the new later point in time.

2. The method according to claim 1, further comprising setting a time interval between generating an image using the first and second x-ray device such that one image is alternately generated using the first and second x-ray device at regular time intervals for each x-ray device.

3. The method according to claim 1, wherein the tracked object is a marking implant.

4. The method according to claim 3, wherein the marking implant moves in correlation with a breathing motion of a patient.

5. The method according to claim 1, wherein the tracked object is a body structure or body landmark that can be mapped using x-rays.

6. The method according to claim 5, wherein the body structure or body landmark moves in correlation with a breathing motion of a patient.

7. The method according to claim 1, further comprising:
comparing the length of the minimum transversal with a predetermined threshold value;
assuming a state of imprecision when the minimum transversal is greater than the threshold value; and
if a state of imprecision is assumed, compensating for the imprecision.

8. The method according to claim 7, wherein compensating includes increasing a scanning rate of the x-ray devices to compensate for the imprecision.

9. The method according to claim 8, wherein increasing the scanning rate is implemented by reducing the time intervals between generating an image using the first and second x-ray device.

10. The method according to claim 1, further comprising:
comparing the length of the minimum transversal with a predetermined threshold value; and
when the minimum transversal is greater than the threshold value, outputting an error message.

11. A computer program embodied on a computer readable medium for non-diagnostic, stereoscopic x-ray tracking of moving objects in the context of radiotherapy and radiosurgery, wherein first and second x-ray devices are used to repeatedly record x-ray images of an object along two different point of views through a target area of an irradiating apparatus, said two different point of views intersecting at a known angle, comprising:
logic that controls the first and second x-ray devices such that each x-ray device alternately obtains an image of the object as the object moves through the target area, and with the assistance of a computer
logic that determines a first surface that is spanned by a first viewing line from the first x-ray device to the object in an image recorded at an earlier point in time and a second viewing line from the first x-ray device to the object in an image recorded at a later point in time;
logic that determines a first intersecting point from a third viewing line from the second x-ray device to the object in an image recorded at a point in time between the earlier point in time and the later point in time, and the first spanned surface;
logic that determines a second surface, wherein the later point in time becomes a new earlier point in time, and wherein said second surface is spanned by the second viewing line from the first x-ray device to the object in an image recorded at the new earlier point in time and a fourth viewing line from the first x-ray device to the object in an image recorded at a new later point in time;
logic that determines a second intersecting point from a fifth viewing line from the second x-ray device to the object in an image recorded at a point in time between the new earlier point in time and the new later point in time, and the second spanned surface;
logic that calculates a spatial straight connecting line that connects the first and second intersecting points;
logic that calculates a minimum transversal between the spatial straight connecting line and the fourth viewing line of the object at the new later point in time; and
logic that approximates a three-dimensional position of the tracked object from an intersecting point of the minimum transversal and the fourth line of site at the new later point in time.

12. A stereoscopic x-ray tracking device for tracking moving objects in the context of radiotherapy and radiosurgery, comprising:
two x-ray devices operative to repeatedly record x-ray images of an object along two different points of view through the target area of an irradiating apparatus, said points of view intersecting at a known angle,
a controller operative to alternately activate the x-ray devices such that each x-ray device alternately obtains an image of the object as the object moves through the target area; and
a computer-assisted image processing device operative to:
determine a first surface that is spanned by a first viewing line from the first x-ray device to the object in an image recorded at an earlier point in time and a second viewing line from the first x-ray device to the object in an image recorded at a later point in time;
determine a first intersecting point from a third viewing line from the second x-ray device to the object in an image recorded at a point in time between the earlier point in time and the later point in time, and the first spanned surface;
determine a second surface, wherein the later point in time becomes a new earlier point in time, and wherein said second surface is spanned by the second viewing line from the first x-ray device to the object in an image recorded at the new earlier point in time and a fourth viewing line from the first x-ray device to the object in an image recorded at a new later point in time;
determine a second intersecting point from a fifth viewing line from the second x-ray device to the object in an image recorded at a point in time between the new earlier point in time and the new later point in time, and the second spanned surface;
calculate a spatial straight connecting line that connects the first and second intersecting points;
calculate a minimum transversal between the spatial straight connecting line and the fourth viewing line of the object at the new later point in time; and
approximate a three-dimensional position of the tracked object from an intersecting point of the minimum transversal and the fourth line of site at the new later point in time.

* * * * *